US010959967B2

(12) United States Patent
Kohli et al.

(10) Patent No.: US 10,959,967 B2
(45) Date of Patent: Mar. 30, 2021

(54) EFFERVESCENT COMPOSITIONS

(75) Inventors: Rajnish Kohli, Hillsborough, NJ (US); Richard Scott Robinson, Belle Mead, NJ (US); Ralph Peter Santarpia, III, Edison, NJ (US); James R. Brown, Edison, NJ (US); Richard J. Sullivan, Atlantic Highlands, NJ (US); Michael Prencipe, Princeton Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 1169 days.

(21) Appl. No.: 12/866,609

(22) PCT Filed: Feb. 6, 2009

(86) PCT No.: PCT/US2009/033299
§ 371 (c)(1),
(2), (4) Date: Aug. 6, 2010

(87) PCT Pub. No.: WO2009/100272
PCT Pub. Date: Aug. 13, 2009

(65) Prior Publication Data
US 2010/0322985 A1 Dec. 23, 2010

Related U.S. Application Data

(60) Provisional application No. 61/027,430, filed on Feb. 8, 2008.

(51) Int. Cl.
| | | |
|---|---|---|
| A61K 31/19 | (2006.01) | |
| A61Q 11/00 | (2006.01) | |
| A61K 8/44 | (2006.01) | |
| A61K 9/46 | (2006.01) | |
| A61K 9/20 | (2006.01) | |

(52) U.S. Cl.
CPC ............... *A61K 31/19* (2013.01); *A61K 8/44* (2013.01); *A61K 9/0007* (2013.01); *A61Q 11/00* (2013.01); *A61K 9/2009* (2013.01); *A61K 9/2013* (2013.01); *A61K 2800/222* (2013.01)

(58) Field of Classification Search
None
See application file for complete search history.

(56) References Cited

U.S. PATENT DOCUMENTS

| | | |
|---|---|---|
| 3,535,421 A | 10/1970 | Briner et al. |
| 3,678,154 A | 7/1972 | Widder et al. |
| 3,772,431 A * | 11/1973 | Mlkvy ............... A61K 8/19 424/44 |
| 3,903,255 A | 9/1975 | Gusman et al. |
| 3,925,543 A | 12/1975 | Donohue |
| 3,932,605 A | 1/1976 | Vit |
| 3,932,608 A | 1/1976 | Anderson et al. |
| 3,943,241 A | 3/1976 | Anderson et al. |
| 3,988,434 A | 10/1976 | Schole et al. |
| 4,011,309 A | 3/1977 | Lutz |
| 4,022,880 A | 5/1977 | Vinson et al. |
| 4,025,616 A | 5/1977 | Haefele |
| 4,042,680 A | 8/1977 | Muhler et al. |
| 4,064,138 A | 12/1977 | Saari et al. |
| 4,100,269 A | 7/1978 | Pader |
| 4,108,979 A | 8/1978 | Muhler et al. |
| 4,108,981 A | 8/1978 | Muhler et al. |
| 4,146,607 A | 3/1979 | Ritchey |
| 4,154,813 A | 5/1979 | Kleinberg |
| 4,160,821 A | 7/1979 | Sipos |
| 4,211,341 A * | 7/1980 | Weyn .................... A61K 8/0237 222/94 |
| 4,216,961 A | 7/1980 | Curtis et al. |
| 4,225,579 A | 9/1980 | Kleinberg |
| 4,259,316 A | 3/1981 | Nakashima et al. |
| 4,267,164 A * | 5/1981 | Yeh ......................... A61K 8/21 424/44 |
| 4,269,822 A | 5/1981 | Pellico et al. |
| 4,305,928 A | 12/1981 | Harvey |
| 4,335,102 A | 6/1982 | Nakashima et al. |
| 4,339,432 A | 7/1982 | Ritchey et al. |
| RE31,181 E | 3/1983 | Kleinberg et al. |
| 4,466,954 A | 8/1984 | Ichikawa et al. |
| 4,487,757 A | 12/1984 | Kiozpeoplou |
| 4,528,181 A | 7/1985 | Morton et al. |
| 4,532,124 A | 7/1985 | Pearce |
| 4,538,990 A | 9/1985 | Pashley |
| 4,645,662 A | 2/1987 | Nakashima et al. |
| 4,656,031 A | 4/1987 | Lane et al. |
| 4,725,576 A | 2/1988 | Pollock et al. |
| 4,885,155 A | 12/1989 | Parran et al. |

(Continued)

FOREIGN PATENT DOCUMENTS

| | | |
|---|---|---|
| CN | 1266652 | 9/2000 |
| CN | 101077339 | 11/2007 |

(Continued)

OTHER PUBLICATIONS

Machado et al. CaviStat Confection Inhibition of Caries in Posterior Teeth, Abstract, 83rd Session of the American Association for Dental Research, Mar. 21-24, 2007, New Orleans, LA.

Chatterjee et al,. Bacterial Acidification and CaviStat Alkalinization of Occlusal Fissure pH, Abstract, 83rd Session of the American Association for Dental Research, Mar. 9-12, 2005, Baltimore, MD.

Kleinberg I., A Mixed-Bacteria Ecological Approach to Understanding the Role of the Oral Bacteria in Dental Caries Causation: An Alternative to Streptococcus Mutans and the Specific-Plaque Hypothesis, CRIT. Rev. Oral Biol. Med,. 12(2): 108-125 (2002).

Kleinberg I., A New Salvia-Based Anticaries Composition, Dentistry Today, vol. 18, No. 2, Feb. 1999.

(Continued)

*Primary Examiner* — Robert T. Crow
*Assistant Examiner* — John P Nguyen

(57) ABSTRACT

The present invention is directed to effervescent compositions comprising a basic amino acid.

11 Claims, No Drawings

(56) References Cited

U.S. PATENT DOCUMENTS

| | | | |
|---|---|---|---|
| 4,997,640 A | 3/1991 | Bird et al. | |
| 5,096,700 A | 3/1992 | Siebel et al. | |
| 5,286,480 A | 8/1994 | Boggs et al. | |
| 5,334,617 A | 12/1994 | Ulrich et al. | |
| 5,370,865 A | 12/1994 | Yamagishi et al. | |
| 5,693,795 A | 6/1997 | Friedman et al. | |
| 5,747,004 A * | 5/1998 | Giani | A61K 8/19 424/49 |
| 5,762,911 A | 6/1998 | Kleinberg et al. | |
| 5,817,294 A * | 10/1998 | Arnold | A61K 8/22 424/44 |
| 5,906,811 A | 5/1999 | Hersh | |
| 5,922,346 A | 7/1999 | Hersh | |
| 5,925,378 A | 7/1999 | Carnazzo | |
| 5,997,301 A | 12/1999 | Linden | |
| 6,217,851 B1 * | 4/2001 | Kleinberg | A61K 8/19 424/49 |
| 6,436,370 B1 * | 8/2002 | Kleinberg et al. | 424/49 |
| 6,488,961 B1 * | 12/2002 | Robinson et al. | 424/466 |
| 6,524,588 B1 | 2/2003 | Kleinberg et al. | |
| 6,805,883 B2 | 10/2004 | Chevaus et al. | |
| 7,815,897 B1 * | 10/2010 | Wehling | A61K 9/0007 424/401 |
| 2002/0081360 A1 | 6/2002 | Burgard et al. | |
| 2002/0127184 A1 * | 9/2002 | Selim | A61K 9/0007 424/44 |
| 2002/0131987 A1 | 9/2002 | Carnazzo | |
| 2003/0099760 A1 | 5/2003 | Okai | |
| 2003/0170301 A1 | 9/2003 | Wehling | |
| 2007/0154863 A1 | 7/2007 | Cai et al. | |
| 2007/0184826 A1 | 8/2007 | Won-Hyoung et al. | |

FOREIGN PATENT DOCUMENTS

| | | |
|---|---|---|
| DE | 19800812 | 7/1999 |
| FR | 2786395 | 6/2000 |
| GB | 1178294 | 1/1970 |
| GB | 1321419 | 6/1973 |
| JP | 07-258053 | 10/1995 |
| JP | H0958053 | 3/1997 |
| JP | 2001-089337 | 4/2001 |
| WO | WO 01/22917 | 4/2001 |
| WO | WO 01/52803 | 7/2001 |
| WO | WO 2003/026610 | 4/2003 |
| WO | WO 2005/099658 | 10/2005 |
| WO | WO 2007/075408 | 7/2007 |

OTHER PUBLICATIONS

Acevedo et al., "The Inhibitory effect of an arginine bicarbonate/calcium carbonate (CaviStat)-containing dentifrice on the develpoment of dental caries in Venezuelean school children", The Journal of clinical Dentistry, 2005, v.16, No. 3, pp. 63-70, ISSN 0895-8831.

"Neutraceutics—Symbiotropin Berry Effervescent 40 Packets," Nutrition Express Website (Oct. 3, 2006).

Anonymous, "A Review of Patents on Effervescent Granules," (http://www.pharmainfo.net/reviews/review-patents-effervescent-granules).

* cited by examiner

EFFERVESCENT COMPOSITIONS

This application claims the benefit of U.S. Patent Application Ser. No. 61/027,430 filed Feb. 8, 2008, the contents of which are incorporated herein by reference.

FIELD OF THE INVENTION

The invention relates to effervescent oral care compositions comprising a basic amino acid.

BACKGROUND OF THE INVENTION

Effervescent powders and tablets are well known in the art, and generally "fizz" when added to water. Such effervescent materials have been utilized in various arts for multiple purposes. For example, ALKA-SELTZER from Bayer Corporation may be used to deliver any number of medicaments for various indications, such as headache, indigestion, gas, stomach cramps, and heartburn. The use of effervescent products to orally deliver medicaments orally is advantageous in that there is no need to swallow capsules or capsules, which is a problem for the elderly and young children. Effervescent products may also include flavorings, which can mask the taste of many medicaments. Some studies have also indicated that the use of effervescent powders in the administration of medicaments also results in enhanced absorption of actives.

Effervescence is usually produced by the reaction of an acid with a carbonate salt, to release carbon dioxide. For example, citric acid may react with sodium bicarbonate to form carbon dioxide, water and sodium citrate. Considering the benefits of effervescent products in the delivery of medicaments, it is desirable to develop improvements in such formulations. As existing effervescent formulations may contribute to dental decay, it is desirable to develop effervescent compositions which do not only avoid decay, but may treat or reverse such effects, and treat disorders of the mouth.

SUMMARY OF THE INVENTION

The present invention includes effervescent compositions comprising a physiologically acceptable salt of a basic amino acid, an acid source, and a soluble carbonate salt, wherein when the composition is dissolved in a solvent, e.g., water, carbon dioxide is released, and the amino acid salt is substantially solubilized.

By "soluble carbonate salt" is meant any salt formed by carbonic acid or dissolved carbon dioxide which is sufficiently soluble to react with the acid in the concentrations provided. In aqueous solution, the carbonate ion, bicarbonate ion, carbon dioxide, and carbonic acid form a dynamic equilibrium. The term "carbonate" as used herein thus generally encompasses the bicarbonate ($HCO_3^-$) and carbonate ($CO_3^{2-}$) forms and mixtures thereof, unless otherwise specified. Soluble carbonate salts thus include, e.g., potassium carbonate, potassium bicarbonate, sodium carbonate, and sodium bicarbonate. The present invention includes solid effervescent forms, such as tablets, powders and granulates, as well as effervescent compositions comprising single tube non-aqueous or low water toothpastes and alternatively dual tube or sequestered compositions, wherein the acid and carbonate are kept separate until use.

The invention thus provides in one embodiment, an effervescent product (Composition 1.0) comprising a basic amino acid in free or physiologically acceptable salt form, an acid source, and a soluble carbonate salt.

In some embodiments, the basic amino acid may be in carbonate or bicarbonate salt form, in which case it can also serve as all or part of the soluble carbonate salt component of the invention.

The invention further includes the following Compositions:

1.1 Composition 1.0 wherein the basic amino acid is arginine, lysine, citrullene, ornithine, creatine, histidine, diaminobutanoic acid, diaminoproprionic acid, salts thereof and/or combinations thereof.
1.2 Composition 1.0 or 1.1 wherein the basic amino acid has the L-configuration.
1.3 Any of the preceding compositions is provided in the form of a salt of a di- or tri-peptide comprising the basic amino acid.
1.4 Any of the preceding compositions wherein the basic amino acid is arginine.
1.5 Any of the preceding compositions wherein the basic amino acid is L-arginine.
1.6 Any of the preceding compositions wherein the salt of the basic amino acid is a carbonate.
1.7 Any of the preceding compositions wherein the salt of the basic amino acid is a bicarbonate.
1.8 Any of the preceding compositions wherein the amino acid salt is arginine bicarbonate.
1.9 Any of the preceding compositions wherein the basic amino acid is present in an amount corresponding to about 1 wt. % to about 10 wt. % of the total composition weight, the weight of the basic amino acid being calculated as free base form.
1.10 Any of the preceding compositions wherein the acidic salt is selected from citric acid, malic acid, tartaric acid, adipic acid, and fumaric acid.
1.11 Any of the preceding compositions wherein the acidic salt is citric acid.
1.12 Any of the preceding compositions further comprising a second basic salt basic salt is selected from sodium bicarbonate, potassium bicarbonate, sodium carbonate, and potassium carbonate.
1.13 Any of the preceding compositions wherein the basic salt is potassium bicarbonate.
1.14 Any of the preceding compositions which produces carbon dioxide when dissolved in a solvent, e.g., water.
1.15 Any of the preceding compositions which is edible following dissolution in a solvent, e.g., water.
1.16 Any of the preceding compositions which dissolves in saliva to form carbon dioxide.
1.17 Any of the preceding compositions which dissolves in the oral cavity.
1.18 Any of the preceding compositions further comprising fluoride, or a fluoride ion source.
1.19 Any of the preceding compositions comprising a fluoride ion source selected from stannous fluoride, sodium fluoride, potassium fluoride, sodium monofluorophosphate, sodium fluorosilicate, ammonium fluorosilicate, amine fluoride, ammonium fluoride, and combinations thereof.
1.20 Any of the preceding compositions further comprising an antiseptic or antimicrobial.
1.21 Any of the preceding compositions comprising an antiseptic or antimicrobial selected from triclosan, herbal extracts and essential oils (e.g., rosemary extract, thymol, menthol, eucalyptol, methyl salicylate), bisguanide antiseptics (e.g., chlorhexidine, alexidine or octenidine), quaternary ammonium compounds (e.g., cetylpyridinium chloride), phenolic antiseptics, hexetidine, povidone iodine, delmopinol, salifluor, metal ions (e.g., zinc salts, for example, zinc citrate), sanguinarine, propolis, and antibiotics 1.22 Any of the preceding compositions which is a mouth wash.

1.23 Any of the preceding compositions which is consumable, e.g., edible.

1.24 Any of the preceding compositions which neutralizes stomach acid, e.g., an antacid.

1.25 Any of the preceding compositions further comprising additional ingredients selected from analgesic agents, antipyretic agents, anti-inflammatory agents, opioids, and vitamins.

1.26 Any of the preceding compositions comprising acetylsalicylic acid, ibuprofen, acetaminophen, and medications which are psychotropic, anti-hypertensitive, anti-seizure, amphetamine, anti-microbial, antibiotic, anti-viral, anti-retroviral, anti-fungal, anti-depressant, stimulants, anti-histamine, anti-anxiety, tricyclics, tranquilizers, benzodiazepines, hypnotics, mood stabilizers, codeine, selective serotonin reuptake inhibitors, anti-allergy, phenothiazine, chemotherapeutics, amines, monoamine oxidase inhibitors, anti-carcinogens, analgesics, muscle relaxants, ergot preparations, anticholinergic, anti-inflammatory, anti-gout preparations, soporific, hormonal preparations, appetite suppressants, analgesics, muscle relaxants, opioids, and combinations thereof.

1.27 Any of the preceding compositions in the form of a powder or granulate.

1.28 Any of the preceding compositions 1.0-1.26 in the form of a dentifrice wherein the acid source is sequestered from the soluble carbonate salt prior to use.

1.29 Composition 1.28 which is a dual component product, such that the component comprising the acid source and the component comprising the soluble carbonate salt are packaged in separate compartments but dispensed together.

1.30 Composition 1.28 which is a low water or water free composition.

Composition 1.28 wherein either the acid source or the soluble carbonate salt is encapsulated such that upon use the encapsulate will break and the acid source and soluble carbonate salt will react to release carbon dioxide. In another embodiment of the present invention, Composition 2.0 is provided comprising any of compositions 1.0-1.26 in the form of a tablet.

The present invention also includes the following compositions:

2.1 Of composition 2.0 further comprising a lubricant 2.2 Of composition 2.0 or 2.1 comprising a lubricant selected from magnesium stearate, sodium benzoate, polyethylene glycol, adipic acid, and combinations thereof.

2.3 Of composition 2.0-2.2 further comprising a binder.

2.4 Of composition 2.0-2.3 comprising a binder selected from dextrose, sorbitol, xylitol, lactose, and combinations thereof.

The present invention also encompasses method 3.0, a method to (i) reduce or inhibit formation of dental caries, (ii) reduce, repair or inhibit pre-carious lesions of the enamel, e.g., as detected by quantitative light-induced fluorescence (QLF) or electrical conductance measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5, (xi) reduce plaque accumulation, (xii) clean the teeth and oral cavity, (xiii) immunize the teeth against cariogenic bacteria, (xiv) reduce erosion, (xv) enhance systemic health, and/or (xvi) treat or inhibit dry mouth, comprising applying a Composition of the Invention to the oral cavity, e.g., by applying a Composition of the Invention to the oral cavity of a patient in need thereof.

The invention also comprises the following methods:

3.1 Method 3.0 wherein the composition of 1.0-2.4 is dissolved in a solvent prior to applying to the oral cavity.

3.2 Of any of the preceding methods wherein the composition of 1.0-2.4 is dissolved in water.

3.3 Of any of the preceding methods wherein the composition of 1.0-2.4 is dissolved in saliva in the oral cavity.

3.4 Of any of the preceding methods wherein the composition of 1.0-2.4 is held in the oral cavity for at least 5 seconds and then expelled.

3.5 Of any of the preceding methods wherein the composition of 1.0-2.4 is swallowed.

Other embodiments of the present invention will be apparent to one of skill in the art.

DETAILED DESCRIPTION OF THE INVENTION

Effervescence generally results from the reaction of an acid and a carbonate in water to produce carbon dioxide. The acid may, for example, be selected from organic acids such as citric, malic, tartaric, adipic, and fumaric acid and mixtures thereof. Carbonates include carbonates of amino acids, e.g., arginine bicarbonate, as well as alkali carbonates, e.g., such as sodium bicarbonate, potassium bicarbonate, sodium carbonate, and potassium bicarbonate. It has been surprisingly found that basic amino acids salts may not only be used as a basic salt, but such basic amino acid salts also impart benefits to the oral cavity.

Without intending to be bound by a particular theory, it is believed that basic amino acids in the oral cavity are metabolized by certain types of bacteria, e.g., S. sanguis which are not cariogenic and which compete with cariogenic bacteria such as S. mutans, for position on the teeth and in the oral cavity. The arginolytic bacteria can use arginine and other basic amino acids to produce ammonia, thereby raising the pH of their environment, while cariogenic bacteria metabolize sugar to produce lactic acid, which tends to lower the plaque pH and demineralize the teeth, ultimately leading to cavities. It is believed that use of a Composition of the Invention may lead to a relative increase in the arginolytic bacteria and a relative decrease in the cariogenic bacteria, resulting in a higher plaque pH.

The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of about 7 or greater. Accordingly, basic amino acids include, but are not limited to, arginine, lysine, citrullene, ornithine, creatine, histidine, diaminobutanoic acid, diaminoproprionic acid, salts thereof or combinations thereof. In a particular embodiment, the basic amino acids are selected from arginine, citrullene, and ornithine, preferably, arginine, for example, 1-arginine.

The compositions of the invention are used in the mouth, and optionally may be ingested, and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion. A preferred salt is a bicarbonate, e.g., arginine bicarbonate.

In various embodiments, the basic amino acid is present in an amount of about 0.5 wt. % to about 50 wt. % of the total composition weight, about 1 wt. % to about 10 wt. % of the total composition weight, for example about 1.5 wt. %, about 3.75 wt. %, about 5 wt. %, or about 7.5 wt. % of the total composition weight.

If the effervescent powders of the present invention may optionally include fluoride, or a fluoride ion source e.g., when formulated to be dissolved in a solvent to be used as a mouthwash. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. Thus, such effervescence powders may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g. about 1450 ppm. Fluoride ion sources may be added to the compositions of the invention at a level of about 0.01 wt. % to about 10 wt. % in one embodiment or about 0.03 wt. % to about 5 wt. %, and in another embodiment about 0.1 wt. % about 1 wt. % by weight of the composition in another embodiment. Weights of fluoride salts to provide the appropriate level of fluoride ion will obviously vary based on the weight of the counter ion in the salt.

The effervescent powders of the present invention may also comprise antiseptics and antimicrobial compounds, e.g., triclosan, herbal extracts and essential oils (e.g., rosemary extract, thymol, menthol, eucalyptol, methyl salicylate), bisguanide antiseptics (e.g., chlorhexidine, alexidine or octenidine), quaternary ammonium compounds (e.g., cetylpyridinium chloride), phenolic antiseptics, hexetidine, povidone iodine, delmopinol, salifluor, metal ions (e.g., zinc salts, for example, zinc citrate), sanguinarine, propolis, and antibiotics. Such antiseptics and antimicrobial compounds are desirable when the effervescent powers of the present invention are formulated to dissolve in a solvent to form a mouthwash.

The effervescent powders of the present invention may also include one or more medicaments or other active, e.g., acetylsalicylic acid, acetaminophen, vitamins, and medications which are psychotropic, anti-hypertensive, anti-seizure, amphetamine, anti-microbial, antibiotic, anti-viral, anti-retroviral, anti-fungal, anti-depressant, stimulants, antihistamine, anti-anxiety, tricyclics, tranquilizers, benzodiazepines, hypnotics, mood stabilizers, codeine, selective serotonin reuptake inhibitors, anti-allergy, phenothiazine, chemotherapeutics, amines, monoamine oxidase inhibitors, anti-carcinogens, analgesics, muscle relaxants, ergot preparations, anti-cholinergic, anti-inflammatory, anti-gout preparations, soporific, hormonal preparations, appetite suppressants, analgesics, muscle relaxants, and opioids The effervescent powders of the present invention may also include one or more flavoring agents. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. Various acids and bases to produce effervescence may also be flavoring agents, such as citric acid and malic acid.

The flavoring agent is incorporated in the oral composition at a concentration of about 0.1 to about 5% by weight and about 0.5 to about 1.5% by weight. The dosage of flavoring agent in the individual oral care composition dosage (i.e., a single dose) is about 0.001 to 0.05% by weight and in another embodiment about 0.005 to 0.015% by weight The effervescent powers of the present invention may be compressed into a tablet form, e.g., to create a single dose format to be added to a solvent. Methods of producing tablets, and general tablet compositions are well known in the art. Tablets generally contain a binder, which are known by those of skill in the art. Preferably, the binders are soluble and include, e.g., dextrose, sorbitol, xylitol, and lactose. Preferably, the amount of binder allows for the tablet to be hard enough to handle, soft enough to disintegrate when introduced into a solvent, and dry enough to be stable.

Tablets may also comprise a lubricant to aid in expulsion of the table from a press. Such lubricants are known by those of skill in the art, and include magnesium stearate, sodium benzoate, polyethylene glycol, and adipic acid.

In one embodiment of the present invention, an effervescent tablet may be placed directly into the mouth to dissolve and form a mouth wash.

EXAMPLE 1

A powder composition is formulated in accordance with the following:
Arginine bicarbonate—50% wt.
Citric Acid—50% wt.

EXAMPLE 2

A powder composition is formulated in accordance with the following:

Arginine bicarbonate—40% wt.
Citric Acid—50% wt.
Sodium carbonate—10% wt.

EXAMPLE 3

0.5 grams of acetylsalicylic acid is added to 10 grams of the compositions of Examples 1 or 2, and compressed into a tablet.

EXAMPLE 4

A tablet prepared in accordance with EXAMPLE 2 is allowed to dissolve and effervesce in 20 ml of cold water. The tablet disintegrates within 2 minutes and is consumed by a person.

EXAMPLE 5

Powder compositions are prepared according to the formulations listed in Table 1.

TABLE 1

| Ingredient | 5-A | 5-B | 5-C | 5-D | 5-E | 5-E |
|---|---|---|---|---|---|---|
| Sodium bicarbonate | 10% | 10.5% | | | | |
| Arginine bicarbonate | 10.3% | 20.8% | | 10% | 15.3% | 10.1% |
| L-Arginine | | | 20.0% | 10.3% | 20% | 30% |
| Sodium carbonate | 30.8% | 20% | | | | |
| Potassium Carbonate | | | 26.3% | 26% | 10.2% | 5.4% |
| Sucralose | 0.7% | .6% | .8% | .6% | .8% | .6% |
| SLS | .3% | .2% | .3% | .3% | .3% | .3% |
| CPC | .1% | .1% | | | .1% | |
| Triclosan | | | | | .1% | 0.2% |
| Sodium fluoride | 2.2% | 2.2% | .7% | .7% | | .7% |
| Citric Acid | 38% | 38% | 43.7% | 43.9% | 43.9% | 43.4% |
| Flavoring, color and solvent | 7.6 | 7.6% | 8.2% | 8.2% | 9.3% | 9.3% |

EXAMPLE 6

1 gram of the compositions of EXAMPLE 5 is added to 15 to 30 ml of water. The powders effervesce and dissolve in water within 2 minutes. A person uses the resulting solution as a mouthwash.

EXAMPLE 7

The powders of EXAMPLE 5 are compressed into tablets 3 grams each, with a diameter of 20 mm.

EXAMPLE 8

A tablet of EXAMPLE 7 is dissolved in from about 15-30 ml of water and allowed to effervesce and dissolve. Insoluble particles are allowed to precipitate. A person agitates the solution to suspend insoluble particles to form a mouthwash, and then takes the solution into the oral cavity for 30 seconds before expelling the solution. The person repeats the procedure daily for one month and finds the mouthwash reduces hypersensitivity of the teeth, and treats dry mouth.

EXAMPLE 9

A powder composition having the following formulation is prepared:

Potassium carbonate—20.5%
Citric acid—45.5%
Flavor, color and solvent—3%
SLS—0.5%
Sweetener—0.5%
Basic Amino Acid—30%

EXAMPLE 10

The compositions of EXAMPLE 8 are compressed into a tablets weighing 3 grams each.

EXAMPLE 11

The tablets of EXAMPLE 8 are taken into a person's mouth and allowed to effervesce with liquid, e.g., saliva, in the oral cavity. The person swishes the resultant solution in the mouth for 30 seconds and then expels the solution from the oral cavity.

EXAMPLE 12

An effervescent dual dentifrice composition having the following formulation is prepared:

| | Components | |
|---|---|---|
| Ingredients | A Weight % | B Weight % |
| Glycerine (95%) | 13 | 10 |
| Sorbitol | — | 8 |
| Sodium lauryl sulfate | 3 | — |
| Betaine (30% soln.) | 2 | — |
| Pluronic F-127 | — | 1.5 |
| Xanthan gum | 0.7 | 0.6 |
| Laponite D | — | 0.6 |
| Flavor | 1.15 | 1.15 |
| Sodium fluoride | 0.486 | — |
| Sodium hexafluorosilicate | — | 0.239 |
| Titanium dioxide | 0.3 | — |
| Tetrasodium pyrophosphate | 0.6 | — |
| Sodium, saccharin | 0.3 | — |
| Arginine bicarbonate | 10 | — |
| Silica thickener | 2 | 2.5 |
| Capsaicin (1.0% Soln.) | 2 | — |
| Silica abrasive | 23 | 35 |
| o-Phosphoric acid (70%) | — | 3.4 |
| Sodium acid pyrophosphate | — | 1.5 |
| Blue pigment | — | 0.0125 |
| Deionized water | QS | QS |

Components A and B are packaged so that the phosphoric acid in B does not react with the arginine bicarbonate in A prior to use. When the product is dispensed and used, A and B combined, and carbon dioxide is released.

The invention claimed is:

1. An effervescent oral care composition in the form of a powder or granulate comprising arginine bicarbonate, citric acid, and an additional carbonate salt selected from sodium bicarbonate, potassium bicarbonate, sodium carbonate or potassium carbonate, wherein carbon dioxide is produced when the composition is dissolved in water; wherein the arginine bicarbonate is present in an amount of 10% to 21% by weight of the composition, wherein citric acid is present in an amount of 38% to 45%, and wherein the oral care composition does not contain calcium.

2. The composition of claim 1, wherein the additional carbonate salt is potassium carbonate.

3. The composition of claim 1, further comprising a fluoride source selected from stannous fluoride, sodium fluoride, potassium fluoride, sodium monofluorophosphate, sodium fluorosilicate, ammonium fluorosilicate, amine fluoride, ammonium fluoride, and combinations thereof.

4. The composition of claim 3, wherein the fluoride source is sodium fluoride or stannous fluoride.

5. The composition of claim 3, wherein the fluoride source is present in an amount of 0.03 to 5 wt% of the composition.

6. The composition of claim 1, wherein the composition is water-free.

7. The composition of claim 1, further comprising a flavoring agent.

8. The composition of claim 1, further comprising zinc citrate.

9. An effervescent oral care composition in the form of a powder or granulate consisting of arginine bicarbonate, citric acid, an additional carbonate salt selected from sodium bicarbonate, potassium bicarbonate, sodium carbonate or potassium carbonate; an antimicrobial consisting of zinc salts, a fluoride source selected from stannous fluoride, sodium fluoride, potassium fluoride, sodium monofluorophosphate, sodium fluorosilicate, ammonium fluorosilicate, amine fluoride, ammonium fluoride, and combinations thereof, and a flavoring agent; wherein carbon dioxide is produced when the composition is dissolved in water, wherein the arginine bicarbonate is present in an amount of 10% to 21% by weight of the composition, wherein citric acid is present in an amount of 38% to 45%, and wherein the oral care composition does not contain calcium.

10. The composition of claim 1, further comprising zinc salts.

11. The composition of claim 10, wherein the zinc salts comprise zinc citrate.

* * * * *